United States Patent [19]

Ogawa

[11] Patent Number: 4,881,109
[45] Date of Patent: Nov. 14, 1989

[54] SENSOR USING A FIELD EFFECT TRANSISTOR AND METHOD OF FABRICATING THE SAME

[75] Inventor: Kazufumi Ogawa, Hirakata, Japan

[73] Assignee: Matsushita Electric Industrial Co., Ltd., Osaka, Japan

[21] Appl. No.: 900,629

[22] Filed: Aug. 26, 1986

[30] Foreign Application Priority Data

Aug. 29, 1985 [JP] Japan .................................. 60-190772
Aug. 29, 1985 [JP] Japan .................................. 60-190776

[51] Int. Cl.⁴ ....................... H01L 29/66; H01L 29/96
[52] U.S. Cl. ....................................... 357/25; 357/23.1; 435/176
[58] Field of Search ....................... 357/25, 23.1, 23.5; 435/176, 177, 178, 180, 181; 204/416, 418

[56] References Cited

U.S. PATENT DOCUMENTS

| | | | |
|---|---|---|---|
| 4,020,830 | 5/1977 | Johnson et al. | 357/54 X |
| 4,218,298 | 8/1980 | Shimada et al. | 357/25 X |
| 4,562,157 | 12/1985 | Lowe et al. | 324/71.1 X |
| 4,670,390 | 6/1987 | Antal née Magyar | 435/174 X |
| 4,683,203 | 7/1987 | Anton et al. | 435/176 X |

*Primary Examiner*—Andrew J. James
*Assistant Examiner*—Sara W. Crane
*Attorney, Agent, or Firm*—Wenderoth, Lind & Ponack

[57] ABSTRACT

Disclosed is a sensor using a field effect transistor. The sensor includes a field effect transistor having a gate electrode, a reactive monomolecular film formed on the surface of the gate electrode, and a sensing material fixed on the gate electrode through a reactive monomolecular film by a chemical bond. The sensing material is strongly bonded to the reactive monomolecular film in such manner that the sensing material is kept alive. Thereby, sensitivity of the sensor is improved.

10 Claims, 4 Drawing Sheets

SENSOR USING A FIELD EFFECT TRANSISTOR AND METHOD OF FABRICATING THE SAME

BACKGROUND OF THE INVENTION

This invention relates to a sensor using a field effect transistor, and more particularly to a sensor having enhanced detecting sensitivity by firmly affixing a sensing material to the gate electrode of a field effective transistor and maintaining the sensing material in an active state.

Sensors using field effect transistors are used as pH sensors, various ion sensors, bio-sensors and others. Referring, for example, to a bio-sensor, bio-sensors conventionally known are prepared by the method of fixing protein or enzyme to the surface of a glass electrode, or the method of fixing a sensing material of protein or enzyme on the gate electrode of a field effect transistor (FET). In such conventional methods, however, the fixing method of enzyme or protein was not satisfactory, and the sensitivity was not so high.

That is, in the conventional protein or enzyme fixing method, the enzyme or protein was directly applied to the FET electrode or glass electrode, the protein or enzyme was mixed in the resin and applied, or fixed to the resin particles and applied, or the protein or enzyme was fixed by way of an organic film.

However, in the direct application method, the protein or enzyme was separated during measurement, and the durability was not sufficient, or in the method of mixing protein into resin and applying or fixing it to resin particles and applying, part of the protein or enzyme was deactivated and the activity was lowered, or in the conventional method of fixing the protein by way of an organic film, the activity was also insufficient.

SUMMARY OF THE INVENTION

It is hence a primary object of this invention to present a sensor having a sensing material such as protein and enzyme affixed to the gate electrode surface of a field effect transistor, firmly and keeping an active state.

It is another object of this invention to present a method of fabricating such sensor easily.

These and other objects are accomplished by a sensor which comprises a field effect transistor having a gate electrode, a reactive monomolecular film forming on the surface of said gate electrode, and a sensing material fixed on said gate electrode through said reactive monomolecular film. The sensing material is bonded to said reactive monomolecular film in such manner that said sensing material is kept alive.

In a specific embodiment, the reactive monomolecular film has a vinyl group or acetylene group at its one end, and has a chlorosilane group formed by using a straight chain hydrocarbon molecule. The sensing material is one of proteins and enzymes.

In another specific embodiment, said reactive monomolecular film is replaced by a hydrophilic molecular photosensitive film.

According to the present invention as described herein, the following benefits, among others, are obtained.

(1) A high sensitivity sensor having the sensing material bonded to the gate electrode of a field effect transistor firmly in an active state may be presented.

(2) Such sensor may be manufactured easily and at low cost.

While the novel features of the invention are set forth with particularity in the appended claims, the invention, both as to organization and contents, will be better understood and appreciated, along with other objects and features thereof, from the following detailed description taken in conjunction with the drawings.

BRIEF DESCRIPTION OF THE DRAWINGS

FIG. 1 to FIG. 7 are process charts showing the organization and manufacturing method of a bio-sensor according to a first embodiment of this invention, in which FIG. 3 to FIG. 6 are magnified views on the molecular order of a monomolecular film to compose said bio-sensor;

DETAILED DESCRIPTION OF THE INVENTION

Figure 1:
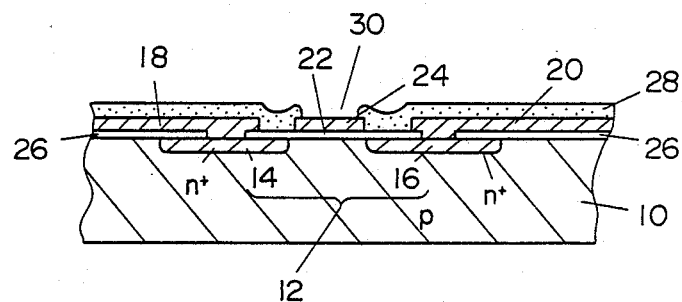

The bio-sensor according to a first embodiment of this invention is described below while referring to FIG. 1 to FIG. 7. As shown in FIG. 1, an FET 12 is preliminarily formed on a p-type semiconductor substrate 10. This FET 12 is formed by a conventional method, and it contains n+ type source, drain regions 14, 16, source, drain electrodes 18, 20, gate oxide film 22, gate electrode 24, and insulation film 26. This semiconductor substrate 10 on which the FET 12 is formed preliminarily is coated with a resist 28, and only the resist on gate electrode 24 is exposed, developed and removed to form an opening 30 (FIG. 1).

Figure 2:
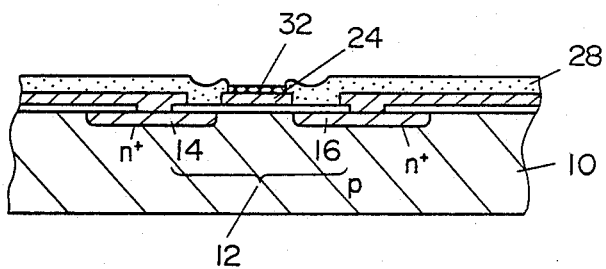

Then, by a chemical adsorption process, a silane surface active agent, such as $CH_2=CH-(CH_2)_n-SiCl_3$ (where n is an integer, of from 0 to 25, preferably from 10 to 20, and $CH_2=CH-$ may be replaced by $CH\equiv C-$), is adsorbed to said opening (FIG. 2).

At this time, on the surface of the gate electrode 24, the oxygen on the metal surface to compose the gate electrode and $-SiCl_3$ of the silane surface active agent selectively react with each other to form a monomolecular film of

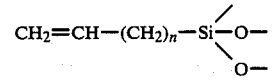

For example, at a concentration of $2.0\times10^{-3}$ to $5.0\times10^{-2}$ mol/liter, when the FET 12 is dipped for 2 or 3 minutes in a solution of surface active agent solution dissolved in a solution of 80% n-hexane, 12% carbon tetrachloride and 8% chloroform, a bond 34 of

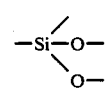

is formed on the metal boundary of the gate electrode 24.

Figure 3:
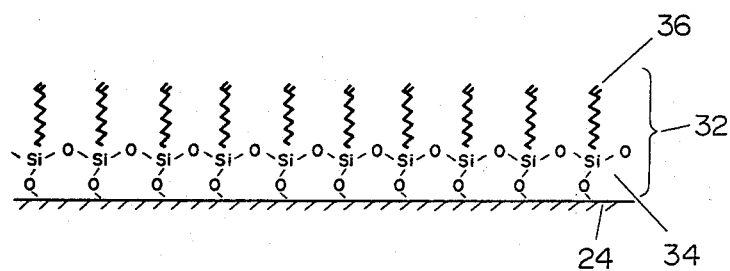
Figure 4:
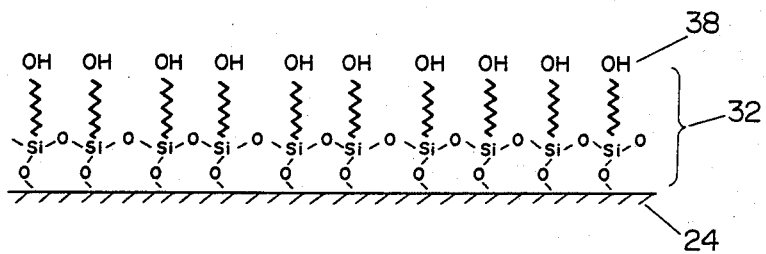

At this time, vinyl groups 36 of the silane surface active agent are orderly arranged on the surface of the gate electrode 24, and a monomolecular film 32 is formed in this state (FIG. 3).

Next, after removing the resist pattern 28 shown in FIG. 2, the substrate on which the monomolecular film 32 is formed is dipped in a THF solution of 1 mol/liter of diborane at room temperature, and it is further dipped in an aqueous solution of 0.1 mol/liter of NaOH and 30% $H_2O_2$, so that a hydroxyl group (—OH) 38 is added to the vinyl groups 36 (or acetylene groups) on the surface of monomolecular film 32.

Figure 5:
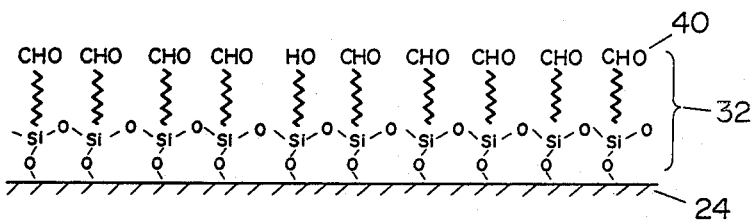

In succession, dipping in a periodate aqueous solution, the OH group on the surface is oxidized into an aldehyde group 40 according to formula (1) (FIG. 5).

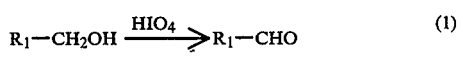
(1)

Furthermore, a protein or an enzyme having a specific activity is fixed by adding and reacting according to formula (2).

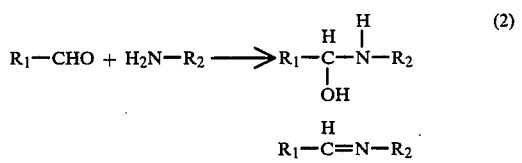
(2)

Figure 6:
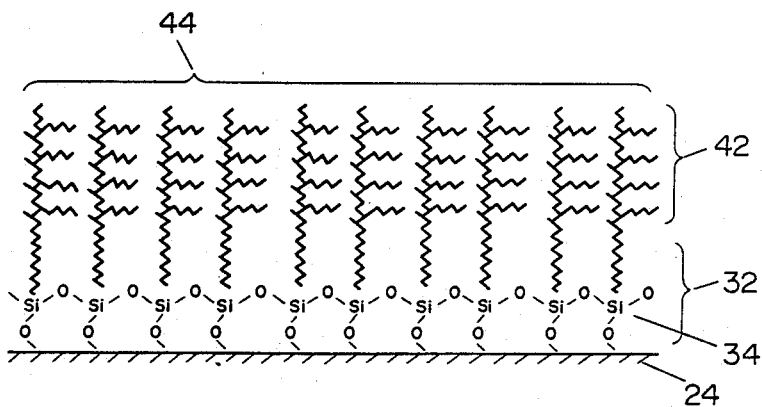
Figure 7:
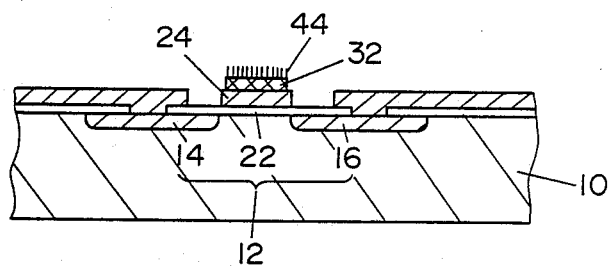

Therefore, the protein or enzyme 42 is firmly fixed on the gate electrode 24, when selecting, through the monomolecular film 32 by chemical reaction, as protein or enzyme film 44 (FIGS. 6, 7).

Finally, when the electrodes are connected and assembled by dicing the substrate, a bio-sensor is completed.

In the above embodiment, an aldehyde method was shown, but the protein or enzyme may be fixed alike by a cyanobromide method as shown in formula (3).

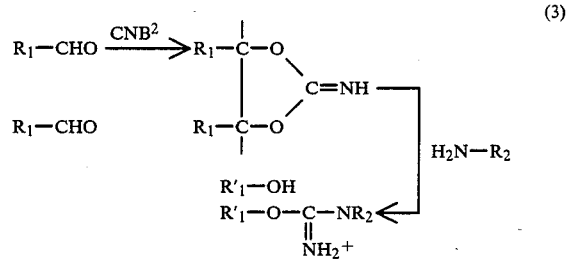
(3)

Or, a chemical adsorption process was employed to form a monomolecular film, but it was confirmed that a monomolecular film may be formed on the gate electrode by Langmuir-Blodgett (LB) method, using $CH_2=CH-(CH_2)_nCOOH$, $CH\equiv C-(CH_2)_nCOOH$, or the like.

Figure 8:
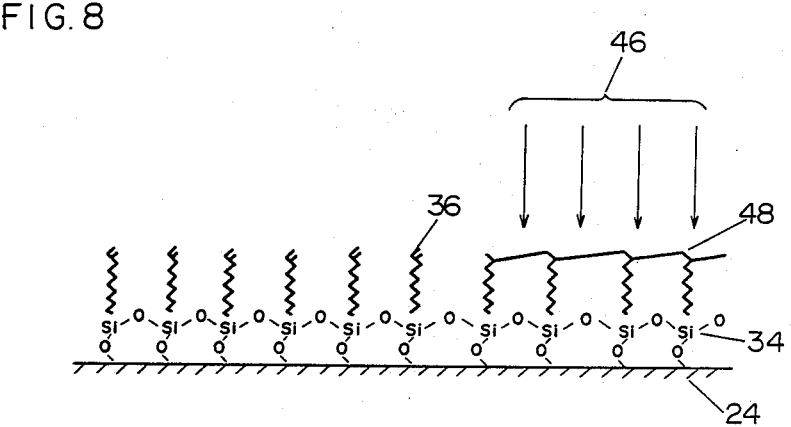
FIG. 8 is a magnified view on the molecular order of a monomolecular film of a bio-sensor according to a second embodiment of this invention.

Furthermore, in the above example, the monomolecular film was formed only on the gate electrode selectively by using the resist 28, but since the vinyl group or acetylene group forms a polymer by its sensitivity to an energy beam, it may be also possible, as a second embodiment of this invention, to manufacture by forming a monomolecular film on the entire surface, exposing it with energy beam 46, leaving only the surface on the gate electrode, to partly deactivate the vinyl group or acetylene group, and adding —OH group to the remaining portion of vinyl group 36 (or acetylene group) (FIG. 8).

It is also clear that the molecular elements may be built up by applying the method of this invention, that is, the self-matching mechanism of protein to the LB film.

Thus, according to the first and second embodiments of this invention, the protein or enzyme may be fixed selectively through the monomolecular film, firmly and without sacrificing the activity of protein or enzyme. Therefore, a bio-sensor or high sensitivity and high reliability may be presented.

Still further, since the manufacturing process is easy, the cost may be reduced greatly.

Figure 9:
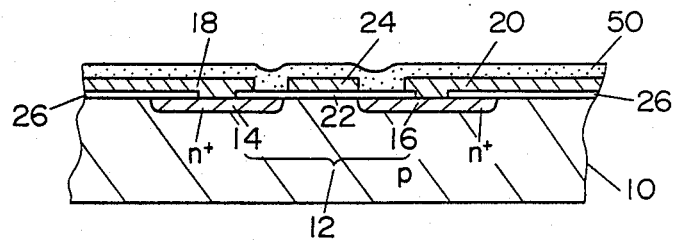
FIG. 9 to FIG. 12 are process charts showing the organization and manufacturing method of a bio-sensor in a third embodiment of this invention.
Figure 10:
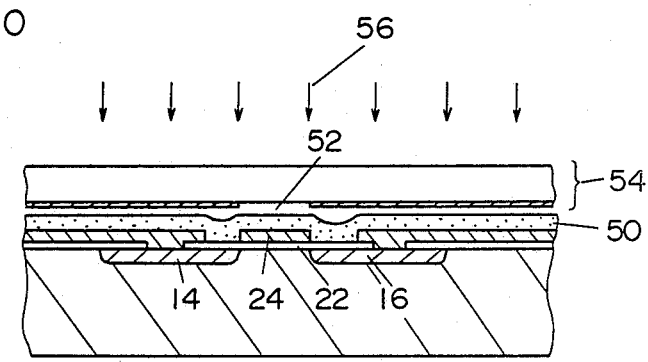
Figure 11:
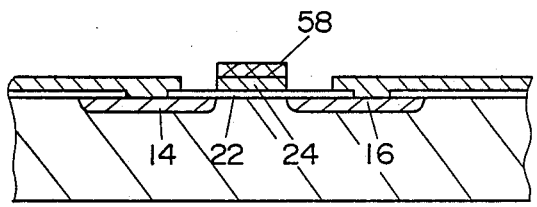

Below is explained the bio-sensor in a third embodiment of this invention in reference to FIG. 9 to FIG. 12. As shown in FIG. 9, a water soluble photosensitive substance (for example, 10 g of pullulan with molecular weight of 200,000, and 1 g of ammonium dichromate, being dissolved in 100 cc of water) is applied on a substrate 10 on which an FET 12 is preliminarily formed, by using a spinner, in a thickness of about 0.5 μm, thereby forming a water-soluble photosensitive thin film 50. Then, by using a photo mask having a desired pattern, for example, a photo mask 54 opened only in the part 52 corresponding to the gate electrode 24, the film is exposed to light rays 56 (FIG. 10) and developed, and a hydrophilic photosensitive film pattern 58 (a thin film pattern left over after exposure and development of water-soluble photosensitive thin film 50) is formed selectively on the gate electrode (FIG. 11).

Then, dipping in a periodate aqueous solution, the OH group on the surface is oxidized into aldehyde according to formula (4) (aldehyde process).

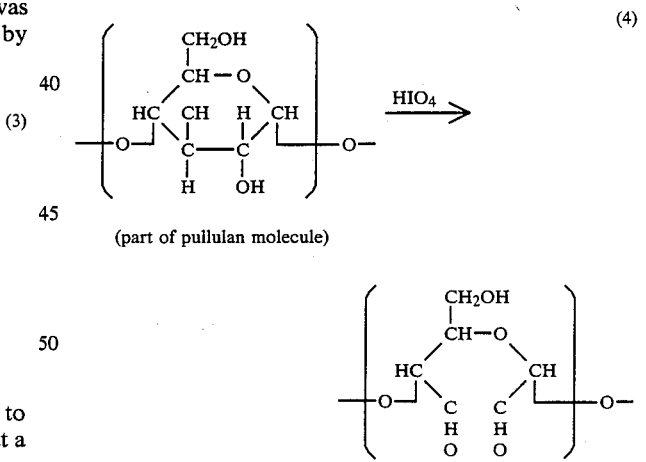
(4)

(part of pullulan molecule)

Furthermore, a protein or an enzyme having a specific activity is added, reacted and fixed according to formula (5).

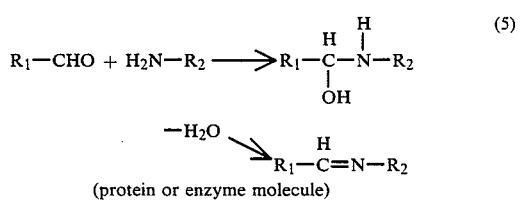
(5)

(protein or enzyme molecule)

Figure 12:
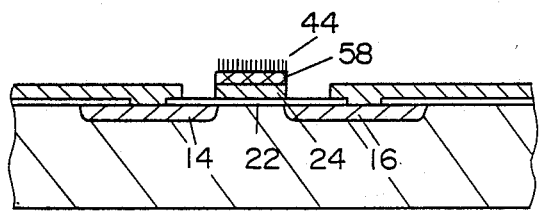

Accordingly, the protein or enzyme is fixed as a protein or enzyme film 44 by chemical reaction selectively with the hydrophilic photosensitive thin film pattern 58 on the gate electrode 24 (FIG. 12).

Finally, by dicing the substrate and connecting and assembling the electrodes, a bio-sensor is completed.

In this embodiment, an aldehyde process was shown, but the protein or enzyme may be similarly fixed by employing a cyanobromide method as shown in formula (6).

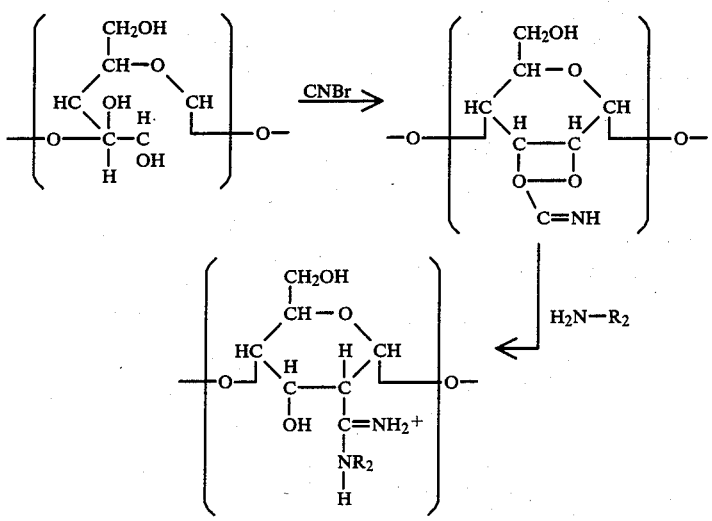

Or, instead of pullulan, polysaccharide such as pectin, protein such as gelatin, casein, or water-soluble polymer such as polyvinyl alcohol and polyvinyl pyrrolidone may be used, and a photosensitive thin film may be similarly formed by adding an optical crosslinking agent, and any other material may be used if having OH group in its molecule, such as novolak resin, etc.

As the optical crosslinking agent, aside from ammonium dichromate, it is possible to use other dichromates, or diazo compound such as diazo resin, or diazide compound such as 4,4'-diazide stylben-2,2'-disulfonicacid sodium salt.

Or when pullulan acetylate having part of pullulan acetylated (degree of replacement 1.5 to 2.5) is used instead of pullulan, it has been confirmed that a similar fixed film may be obtained by using acetone as solvent.

Therefore, according to the third embodiment of this invention, the protein or enzyme may be firmly fixed to the gate electrode of FET selectively, without losing their activity. Besides, since the enzyme or protein is fixed by way of a very thin hydrophilic film, a bio-sensor of high sensitivity and high reliability may be presented.

Besides, the manufacturing process is simple, so that the cost may be reduced significantly.

While specific embodiments of the invention have been illustrated and described herein, it is realized that other modifications and changes will occur to those skilled in the art. It is therefore to be understood that the appended claims are intended to cover all modifications and changes as fall within the true spirit and scope of the invention.

What I claim is:

1. A sensor comprising:
   a field effect transistor having a gate electrode;
   a polymerized monomolecular film with

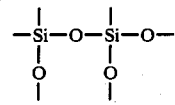

bonds formed selectively on the surface of said electrode; and a monomolecular film of sensing material fixed on said gate electrode through said polymerized monomolecular film by a chemical bond between said sensing material and said polymerized monomolecular film in such a manner that said sensing material is kept active.

2. The sensor of claim 1, wherein said polymerized monomolecular film has straight hydrocarbon chains each of which contains a group of the formula $-(CH_2)_n-$ where n is an integer of 10–20.

3. The sensor of claim 1, wherein said sensing material is a protein or an enzyme.

4. A sensor comprising:
   a field effect transistor having a gate electrode;
   a hydrophilic polymer photosensitive thin film formed selectively on the surface of said gate electrode, wherein said hydrophilic polymer photosensitive thin film is crosslinked with an optical crosslinking agent selected from the group consisting of a dichromate, a diazo compound and a diazide compound; and
   a monomolecular film of sensing material fixed on said gate electrode through said hydrophilic polymer photosensitive thin film by a chemical bond between said sensing material and said hydrophilic polymer photosensitive thin film in such a manner that said sensing material is kept active.

5. The sensor of claim 4, wherein said chemical bond is between said sensing material and a substance having a hydroxyl group or carboxyl group in said hydrophilic polymer photosensitive thin film.

6. The sensor of claim 4, wherein said sensing material is a protein or an enzyme.

7. The sensor of claim 4, wherein said hydrophilic polymer photosensitive thin film contains a polysaccharide, a protein or a water-soluble synthetic polymer.

8. The sensor of claim 7, wherein said hydrophilic polymer photosensitive thin film contains pectin, casein, polyvinyl alcohol or polyvinyl pyrrolidone.

9. The sensor of claim 4, wherein said optical cross-linking agent is ammonium dichromate, a diazo resin or 4,4'-diazidestylben-2,2'-disulfonicacid sodium salt.

10. A sensor comprising:
a field effect transistor having a gate electrode;
a hydrophilic polymer photosensitive thin film formed selectively on the surface of said gate electrode; and
a monomolecular film of sensing material selected from the group consisting of a protein and an enzyme fixed on said gate electrode through said hydrophilic polymer photosensitive thin film by a chemical bond of the formula

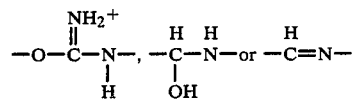

between said sensing material and said hydrophilic polymer photosensitive thin film in such a manner that said sensing material is kept active.

* * * * *